United States Patent [19]

Hanson et al.

[11] Patent Number: 5,639,974

[45] Date of Patent: Jun. 17, 1997

[54] DISSOLUTION TEST APPARATUS

[76] Inventors: Royal A. Hanson; Bruce E. Renslow, both of 9810 Variel Ave., Chatsworth, Calif. 91311

[21] Appl. No.: 625,160

[22] Filed: Apr. 1, 1996

[51] Int. Cl.$^6$ ..................................................... B01F 1/00
[52] U.S. Cl. ............................................. 73/866; 366/207
[58] Field of Search ............................... 73/866; 188/67, 188/166; 248/123.11, 123.2; 366/140, 199, 203, 207, 297

[56] References Cited

U.S. PATENT DOCUMENTS

| | | | |
|---|---|---|---|
| 1,803,446 | 5/1931 | Warrick | 366/207 |
| 2,621,907 | 12/1952 | Maurer et al. | 366/207 |
| 3,467,500 | 9/1969 | Wilkinson et al. | 366/140 |
| 3,674,116 | 7/1972 | Vogeli | 188/67 |
| 3,791,222 | 2/1974 | Goodhart et al. | 73/866 |
| 3,802,272 | 4/1974 | Bischoff et al. | 73/866 |
| 4,647,213 | 3/1987 | Hay, II | 366/199 |
| 4,898,474 | 2/1990 | Lipson | 366/199 |
| 5,403,090 | 4/1995 | Hofer et al. | 366/207 |

Primary Examiner—Robert Raevis
Attorney, Agent, or Firm—Jack C. Munro

[57] ABSTRACT

A dissolution test apparatus which utilizes a fixed base upon which is movably mounted a drive head. The fixed base which supports a plurality of flasks. Mounted within the drive head are a plurality of mixing paddles. The drive head is to be manually movable from the upper position to a lower position. In the lower position each mixing paddle to be located within a flask. Also mounted in the drive head is a plurality of sample tubes with a sample tube to be located in direct juxtaposition to a mixing paddle. Each sample tube is separately movable relative to the drive head. With the drive head in the upper position the mixing paddles are located spaced from their respective flasks. The weight of the drive head is counterbalanced by a counterbalancing weight assembly. A caliper type of braking arrangement is mounted on the drive head and when in the at-rest position the drive head is fixedly positioned relative to the base. Manual release of the braking arrangement will permit the drive head to be moved between the upper and lower positions relative to the base.

2 Claims, 9 Drawing Sheets

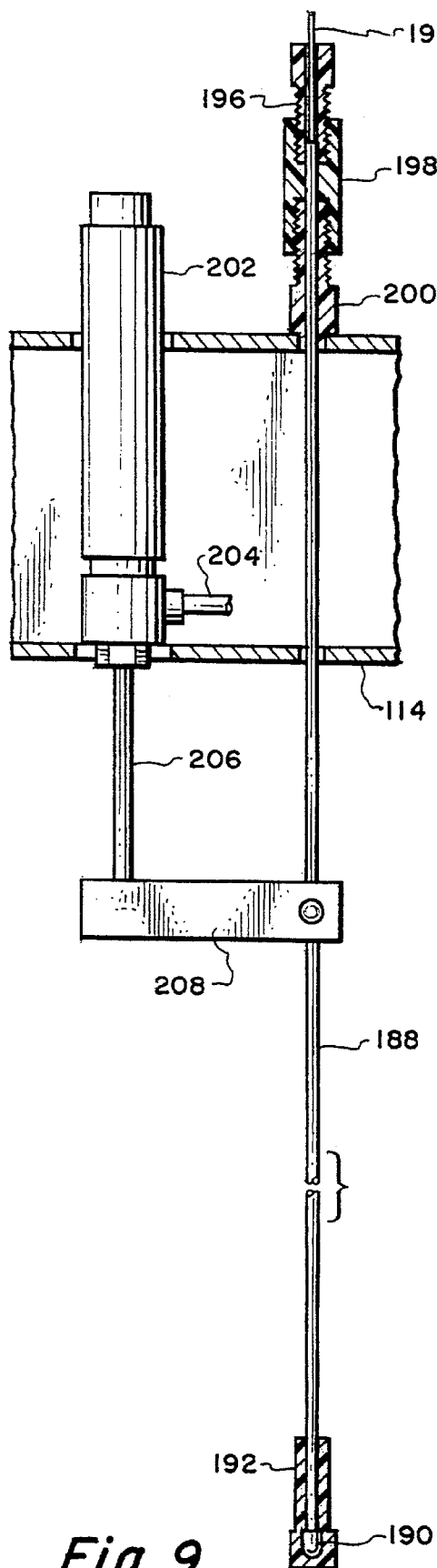
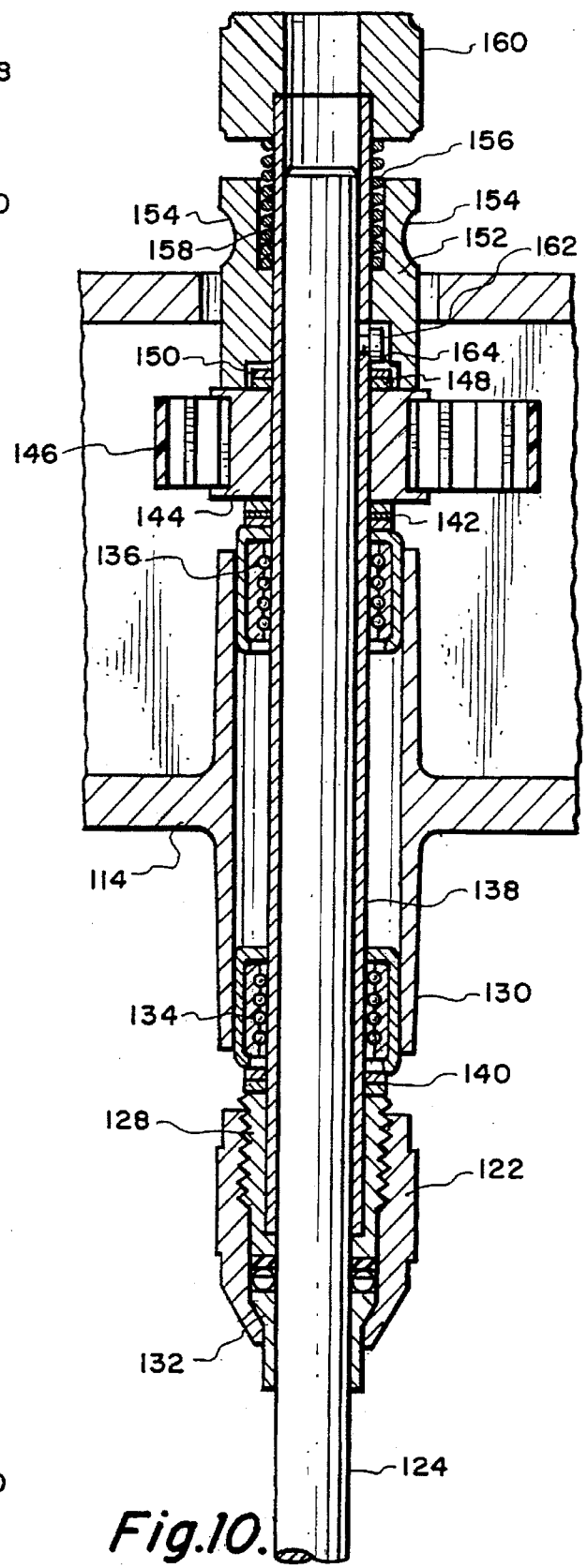
Fig. 9.
Fig. 10.

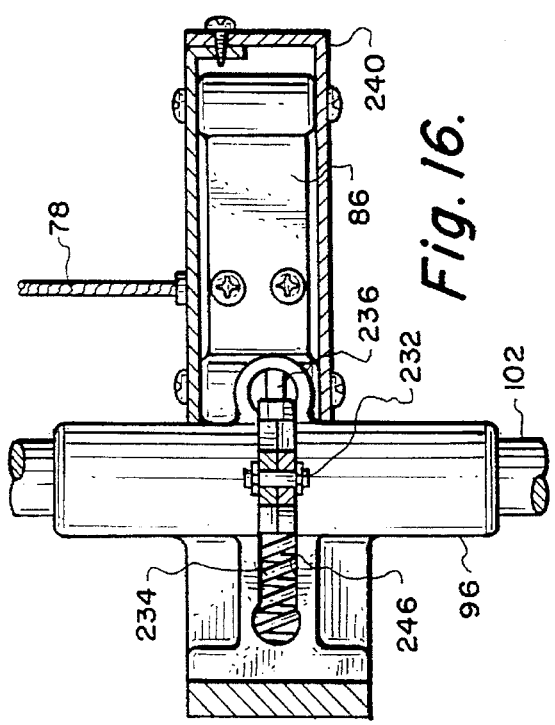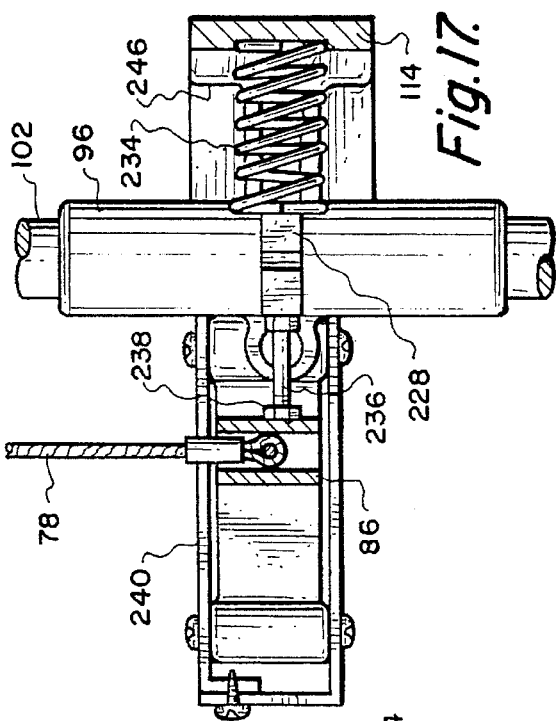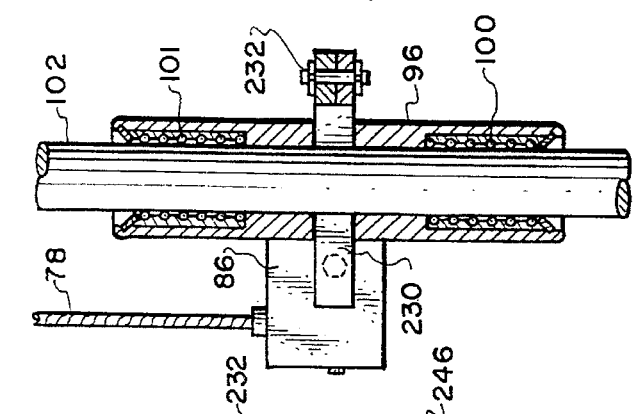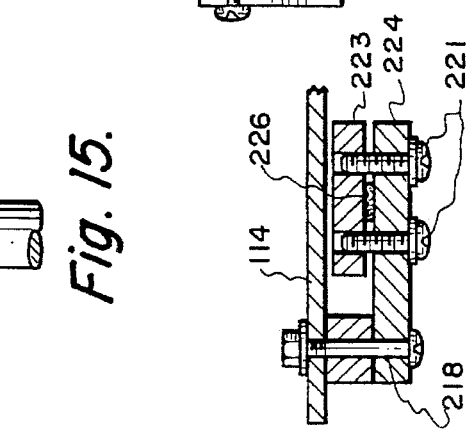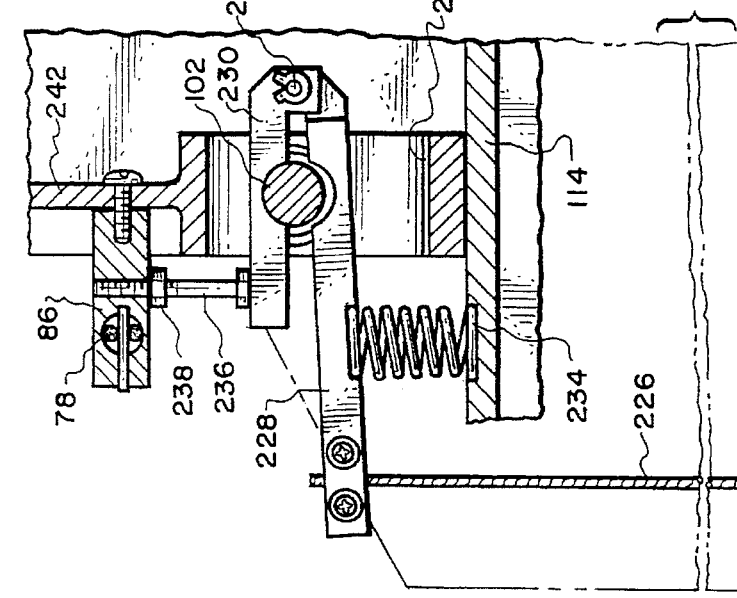

DISSOLUTION TEST APPARATUS

BACKGROUND OF THE INVENTION

1. Field of the Invention

The field of this invention relates to dissolution testing equipment for determining the dissolving rate of drugs encapsulated in the form of a tablet, capsule or caplet which are commonly known as pills.

2. Description of the Prior Art

Drugs are commonly manufactured in the form of pills. The reason for using pills is that when the drug is swallowed by a human, the drug will be disseminated into the body over a period of time as the pill dissolves. Manufacturers of pills are required by law to determine the precise dissolving characteristics of their pill before it is placed on the market. In order to determine the dissolving characteristics, dissolution test equipment are utilized. Although the apparatus is commonly used in conjunction with drugs designed for human consumption, it is considered to be within the scope of this invention to use it with other animals such as horses, cows, rabbits, cats, dogs, monkeys, etc.

Every known form of dissolution testing equipment utilizes one or more of liquid containing flasks. In that flask is to be placed a solution with that solution essentially duplicating the liquid solution that is contained within the stomach of the human body. A precise quantity of the solution is placed within the flask. The pill is then inserted within the flask with the time of the insertion then noted. A mixing paddle is inserted within the flask with mixing at a precise rate then occurring. The mixing procedure is to duplicate the natural turbulence that is created within the stomach of the human. Aliquots are removed from the solution at precise time intervals with these aliquots then being analyzed to determine the amount of drug that has been dissolved within the solution in relation to the time the pill has been in solution.

In order to insure that this testing process is accomplished as accurately as possible, such dissolution testing apparatus in the past has been designed as follows:

1. Normally the dissolution testing apparatus will have a plurality of flasks, such as six or eight. Dissolution testing of the pill is accomplished simultaneously in all six or eight flasks with each flask to receive a pill. The average dissolving rate is then calculated between the flasks.

2. The flasks are placed in a bath with this bath to be maintained at a precise temperature. The temperature level is to essentially duplicate the temperature of the stomach liquid within the human.

3. It is also important to achieve the precise turbulence in each of the flasks with it being understood that if a flask is encountering a greater amount of turbulence, that flask will typically have a faster dissolving rate. Therefore, each mixing paddle that is inserted within a flask must be exactly the same size and it must be precisely centered within that flask. Additionally, each mixing paddle must be rotated at precisely the same speed.

Further, it is desirable for dissolution test equipment to be "user friendly." Dissolution test equipment should be constructed so that it can be operated in a precise manner by relatively unskilled labor. Therefore when using unskilled labor, accurate dissolution test results can be obtained.

Also the operation of the testing equipment must be accomplished with ease and provide the user with the confidence that the tests are performed correctly.

SUMMARY OF THE INVENTION

The dissolution test apparatus of this invention is composed of a fixed base on which is mounted a movable drive head. The base has mounted thereon a plurality of flasks, each to contain a liquid. The drive head includes a plurality of mixing paddles each of which is capable of being rotated at various velocities. Each mixing paddle is to be submergible within a flask. Also mounted on the drive head are a plurality of sampling tubes with there being a sampling tube for each flask. The sampling tubes are to be movable relative to the drive head between an extended position (sampling position) and a retracted position (non-sampling position). There is to be a single sampling tube associated with each mixing paddle with each sampling tube to be partially submergible within its respective flask. The drive head includes a braking device which is manually operated. The braking device when at rest locates the braking device in engagement. Manual release of the braking device will permit movement of the drive head relative to the flask. The drive head is mounted on the base and the weight of the drive head is counterbalanced to the base by means of a counterbalance weight assembly.

BRIEF DESCRIPTION OF THE DRAWINGS

FIG. 9 is a cross-sectional view through a portion of the drive head of the dissolution test apparatus of the present invention showing a sampling tube that is to be used to remove aliquots from a flask taken along line 9—9 of FIG. 4 and also line 9—9 of FIG. 6;

FIG. 10 is a cross-sectional view showing more clearly the structure that rotationally mounts the drive shaft for each mixing paddle taken along line 10—10 of FIG. 4 and also line 10—10 of FIG. 6;

FIG. 13 is a view directed to depicting the braking device that is utilized in conjunction with the dissolution test apparatus of the present invention showing the braking device in its non-braking position;

FIG. 14 is a cross-sectional view through the handle portion of the braking device included in the dissolution test apparatus of the present invention taken along line 14—14 of FIG. 6;

FIG. 15 is a cross-sectional view taken through the caliper braking members and which shows the low frictional bearing arrangement which is used to provide low frictional movement of the drive head relative to the base taken along line 15—15 of FIG. 6;

FIG. 16 is a cross-sectional view through a portion of the calipers of the braking device included within the dissolution test apparatus of the present invention taken along line 16—16 of FIG. 6; and FIG. 17 is a cross-sectional view through the braking device included in the dissolution test apparatus of the present invention taken along line 17—17 of FIG. 6.

DETAILED DESCRIPTION OF THE PREFERRED EMBODIMENT

Figure 1:
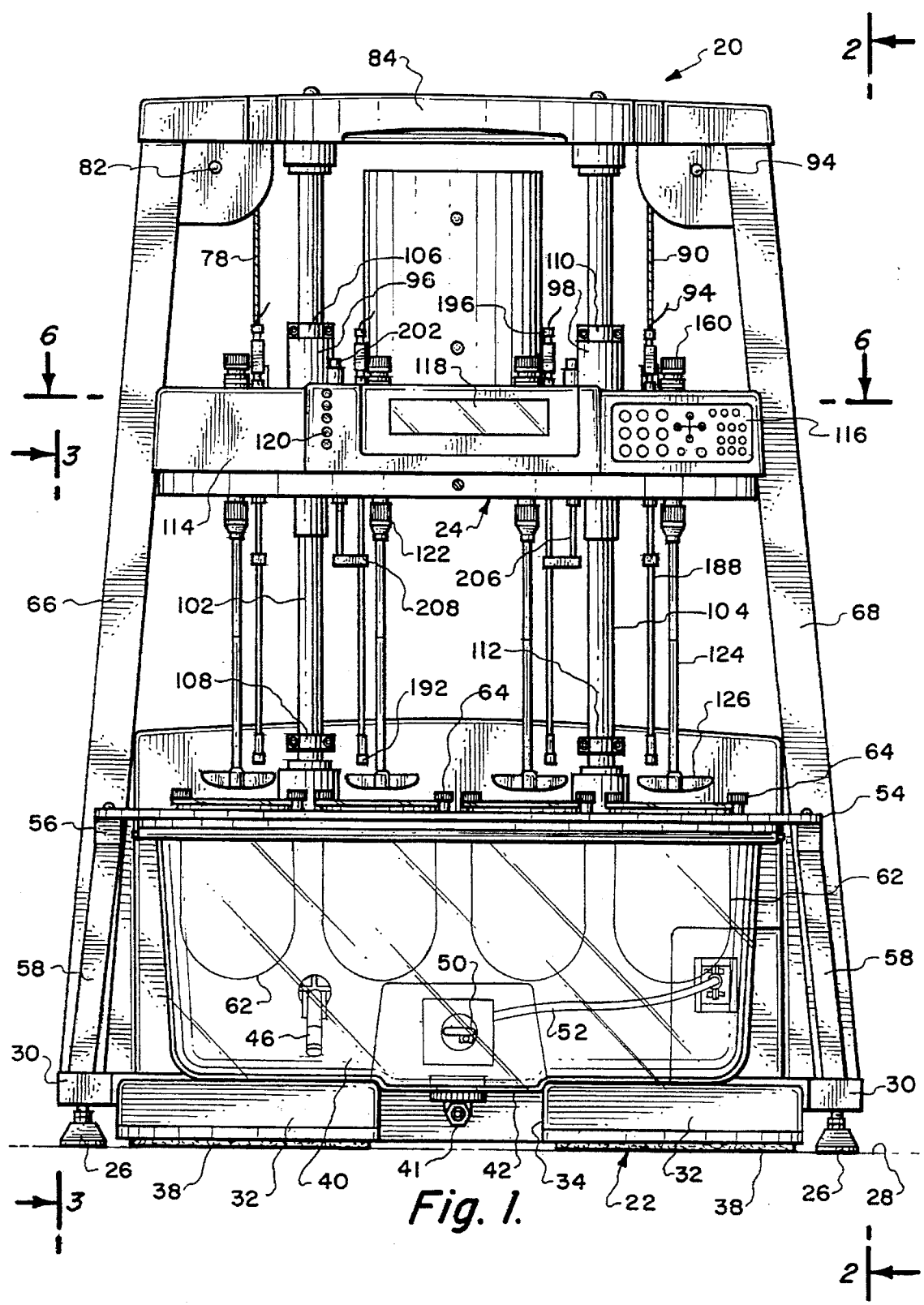
FIG. 1 is a front elevational view of the dissolution test apparatus of the present invention showing the mixing paddles positioned in a displaced position from the flasks that are mounted on the base of the dissolution test apparatus.
Figure 2:
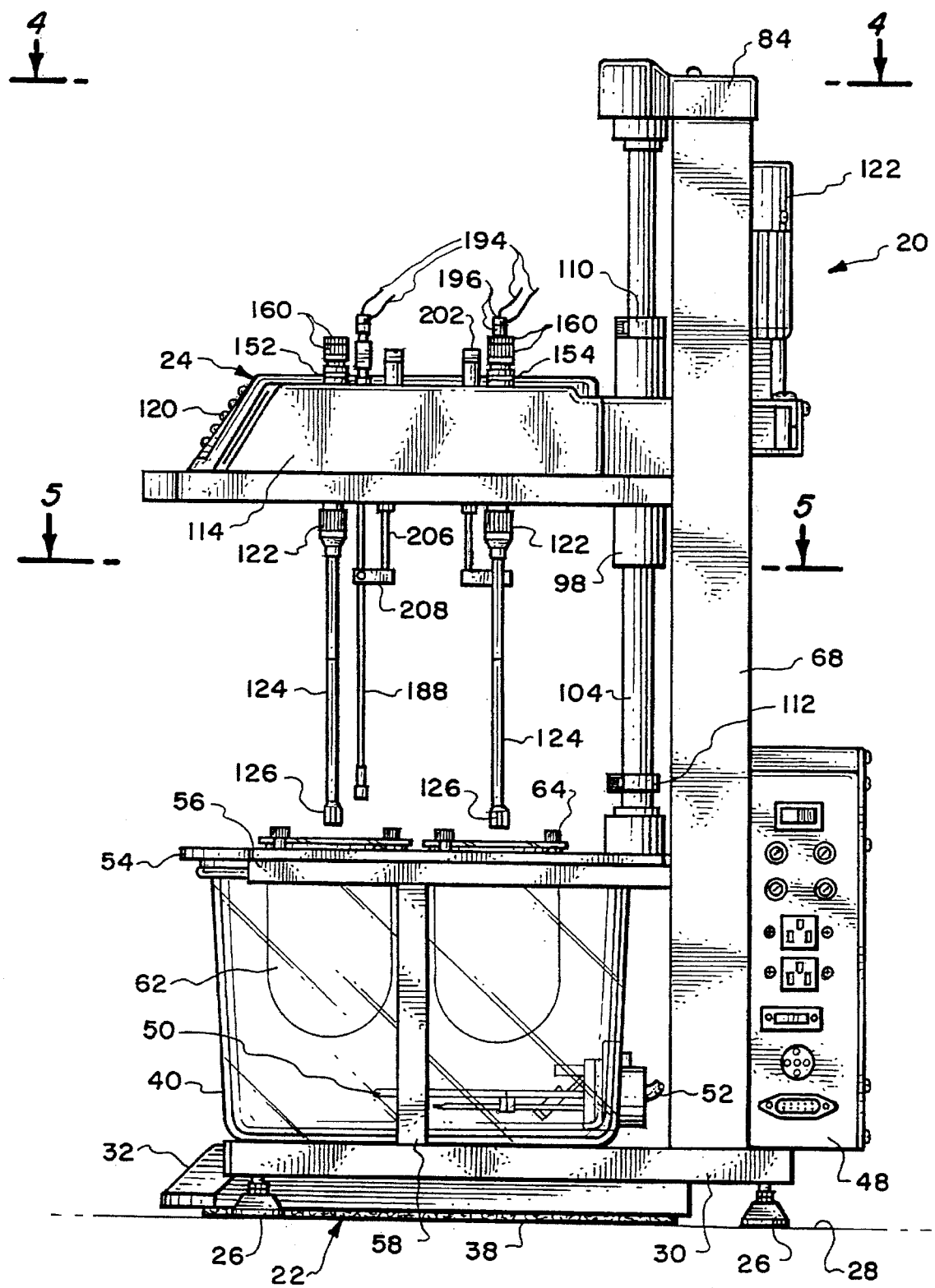
FIG. 2 is a right side elevational view of the dissolution test apparatus of the present invention taken along line 2—2 of FIG. 1.
Figure 3:
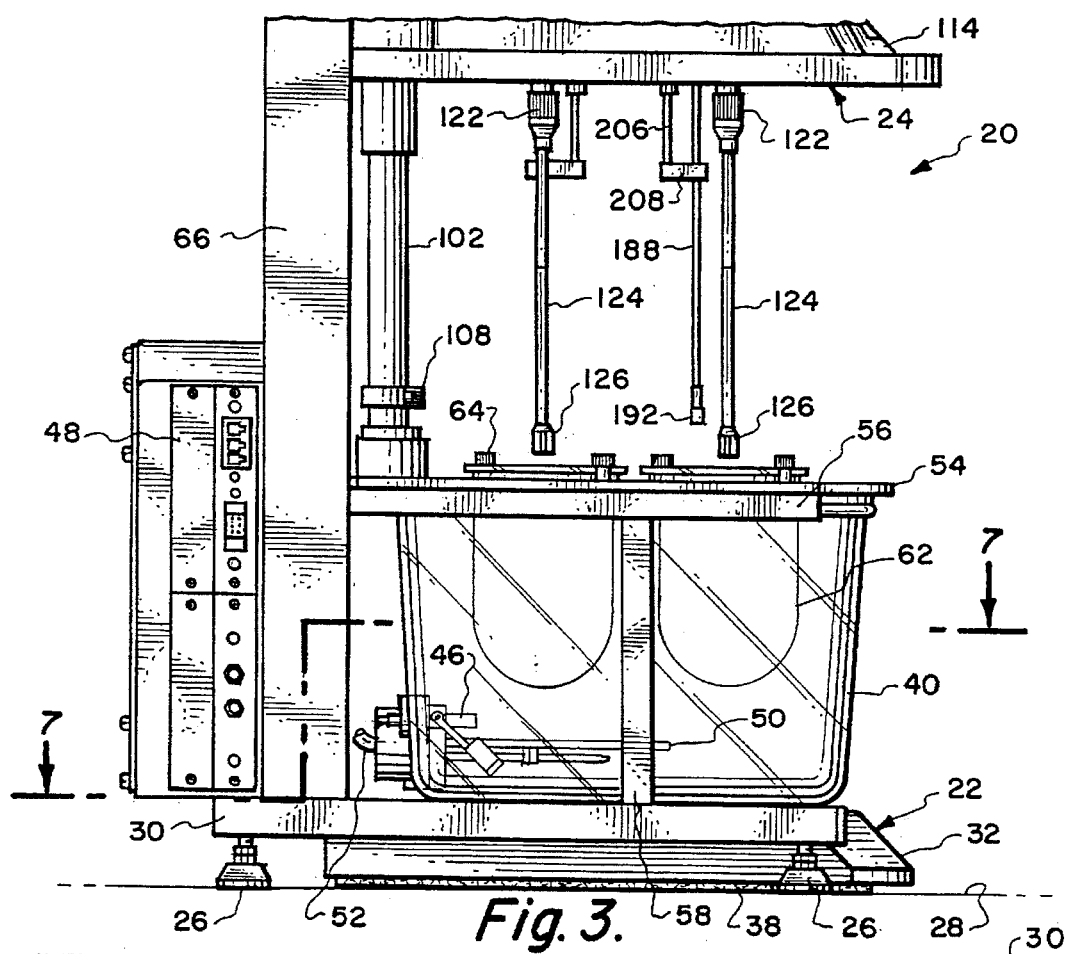
FIG. 3 is a left side elevational view of the dissolution test apparatus of the present invention taken along line 3—3 of FIG. 1.
Figure 7:
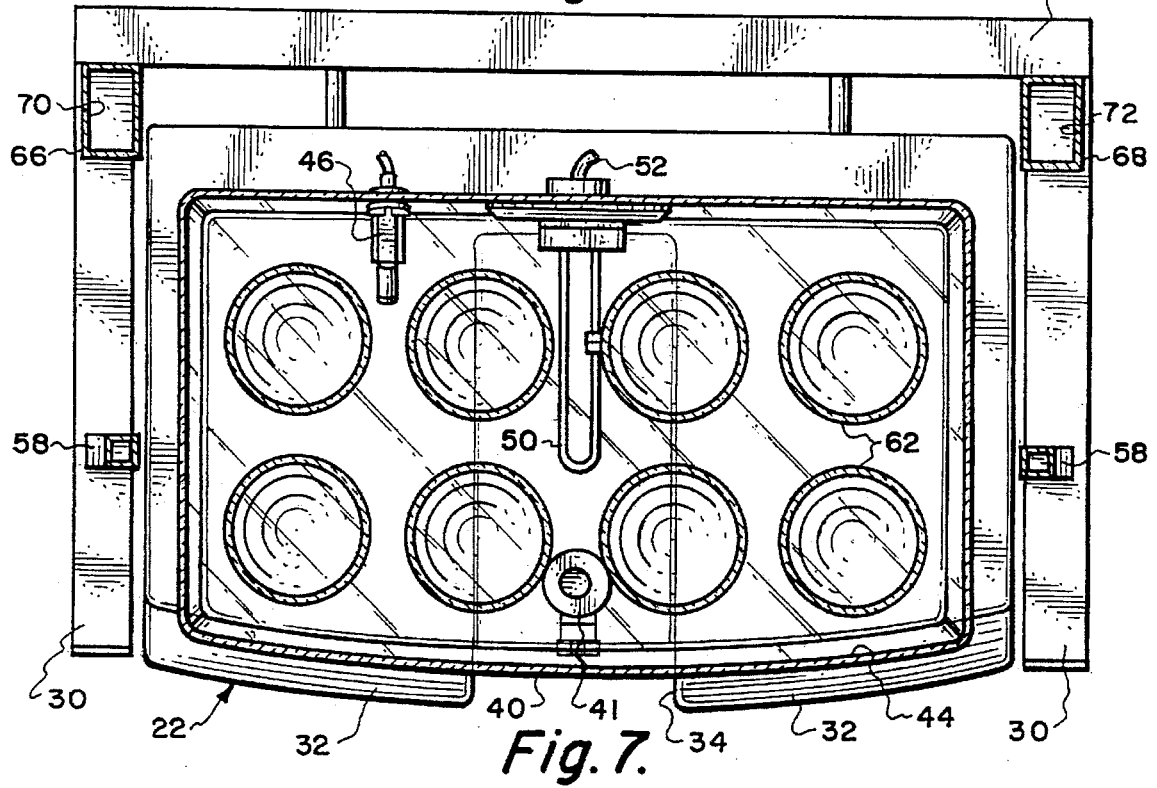
FIG. 7 is a cross-sectional view through the base of the dissolution test apparatus of the present invention taken along line 7—7 of FIG. 3.
Figure 4:
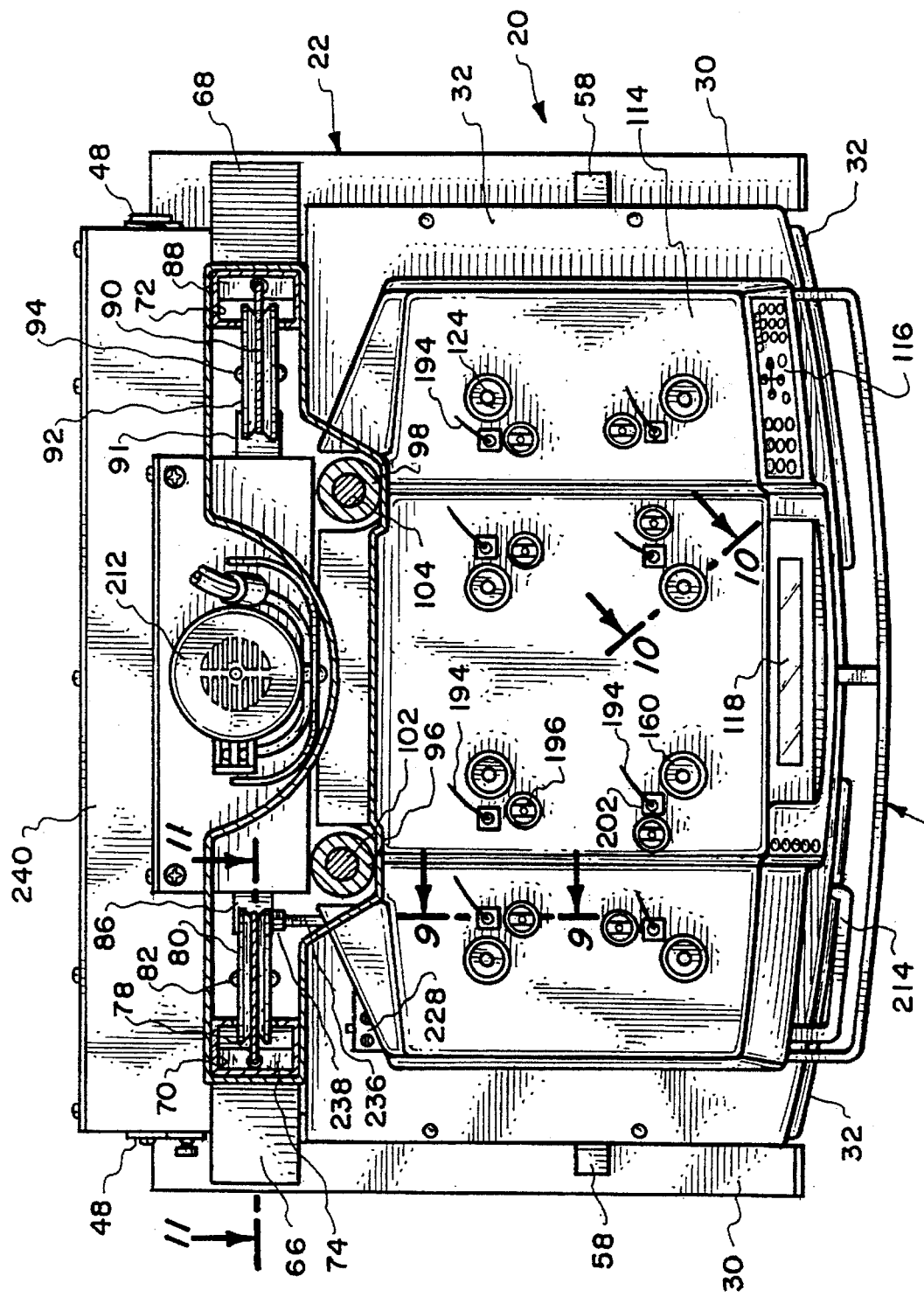
FIG. 4 is a top plan view, partly in cross-section, of the dissolution test apparatus of the present invention taken along line 4—4 of FIG. 2.
Figure 5:
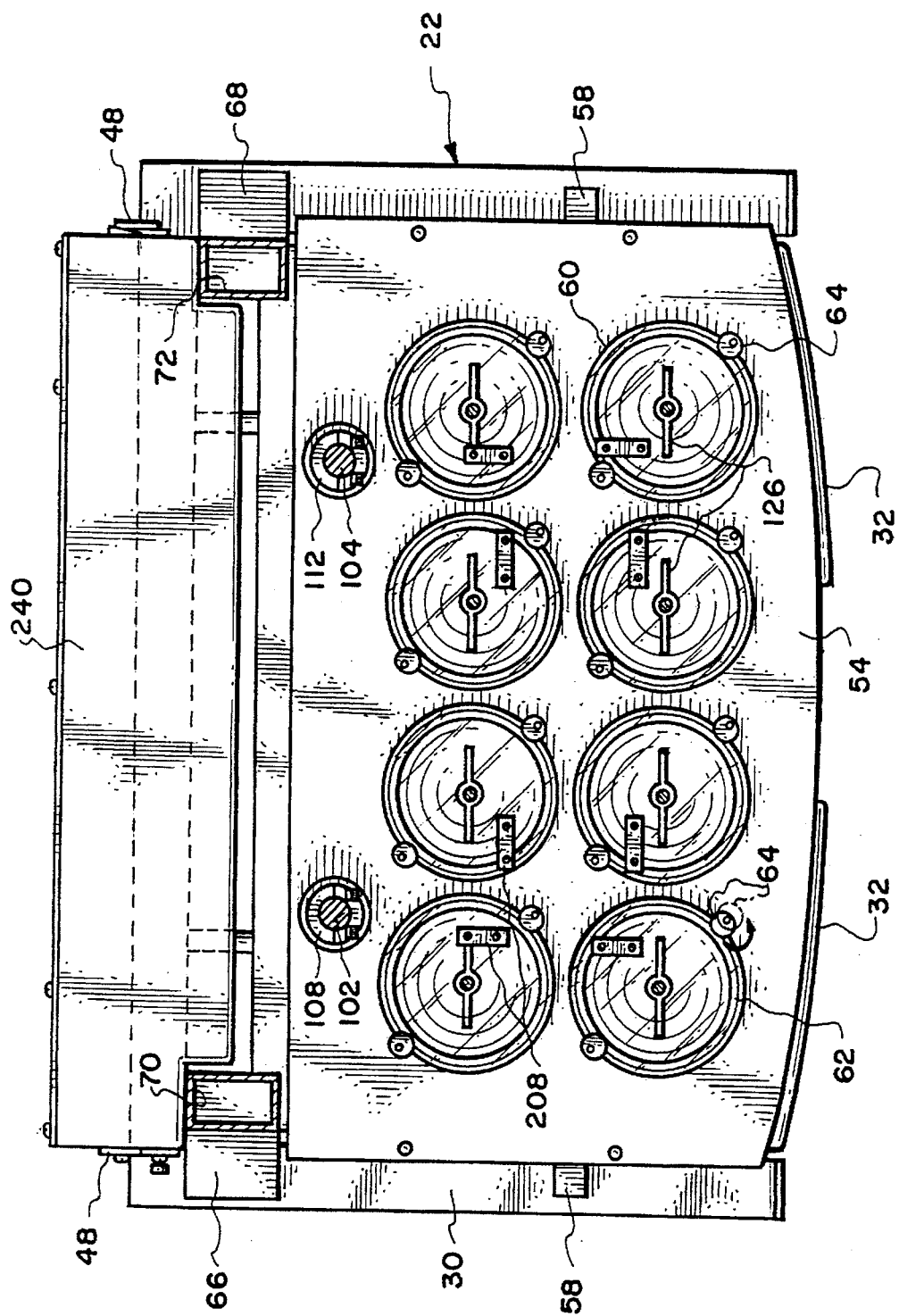
FIG. 5 is a cross-sectional view taken from the top direction of the dissolution test apparatus of the present invention taken along line 5—5 of FIG. 2.
Figure 6:
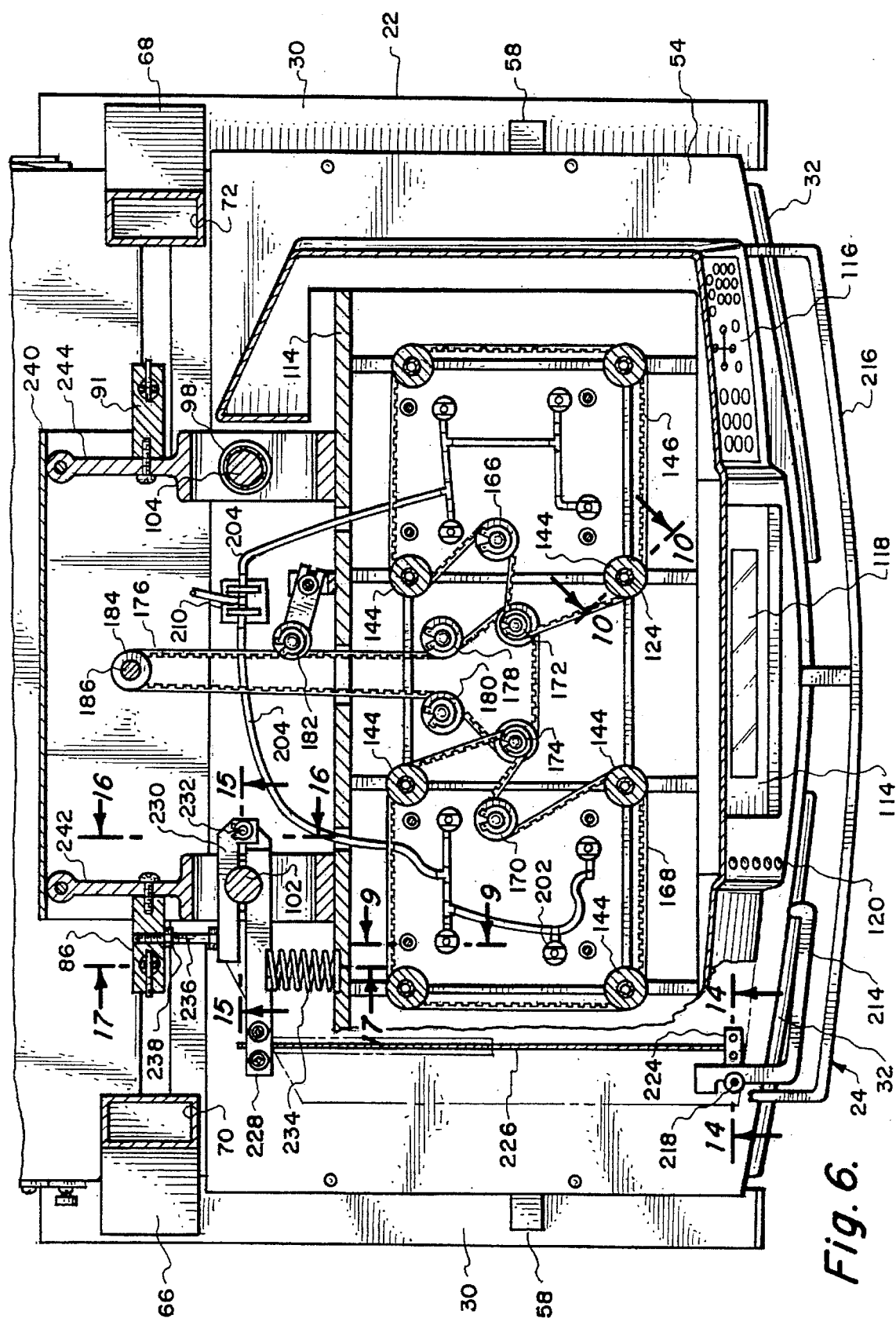
FIG. 6 is a cross-sectional view through the drive head of the dissolution test apparatus of the present invention taken along line 6—6 of FIG. 1 also showing a braking device with this braking device being shown in the braking position.
Figure 8:
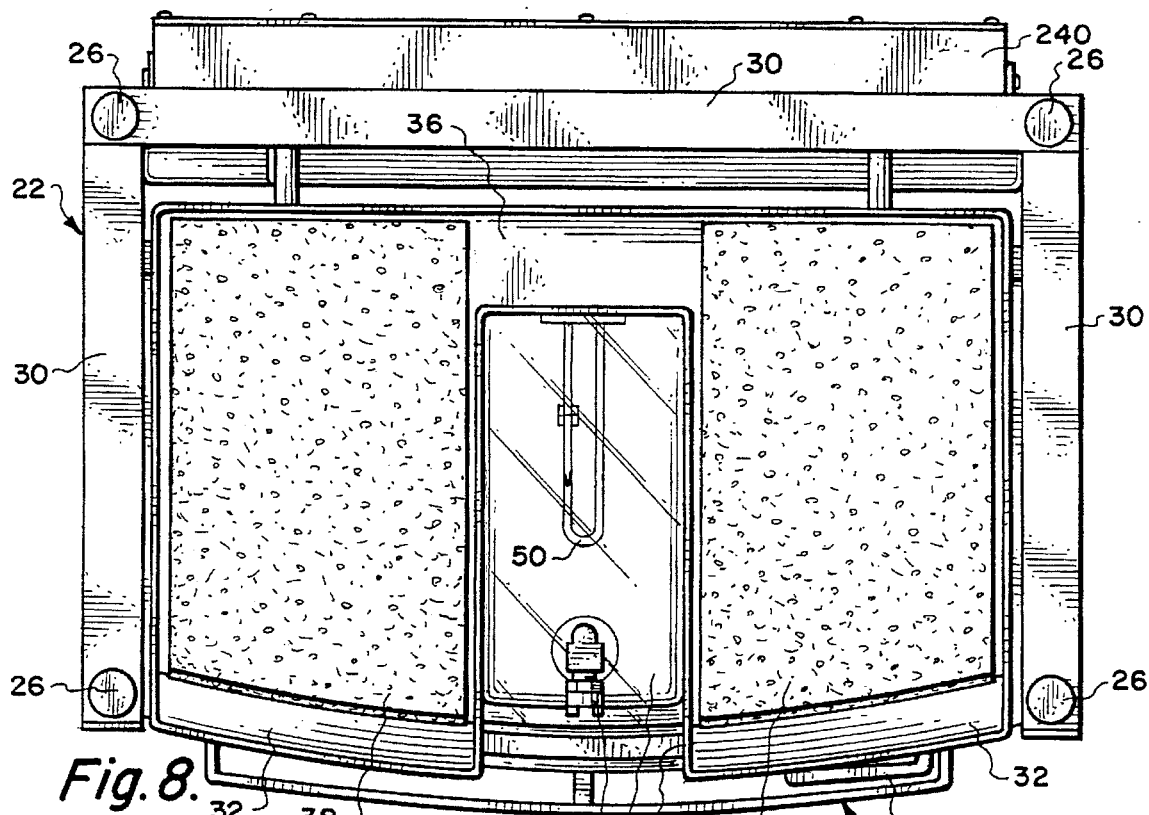
FIG. 8 is a bottom view of the dissolution test apparatus of the present invention.
Figure 11:
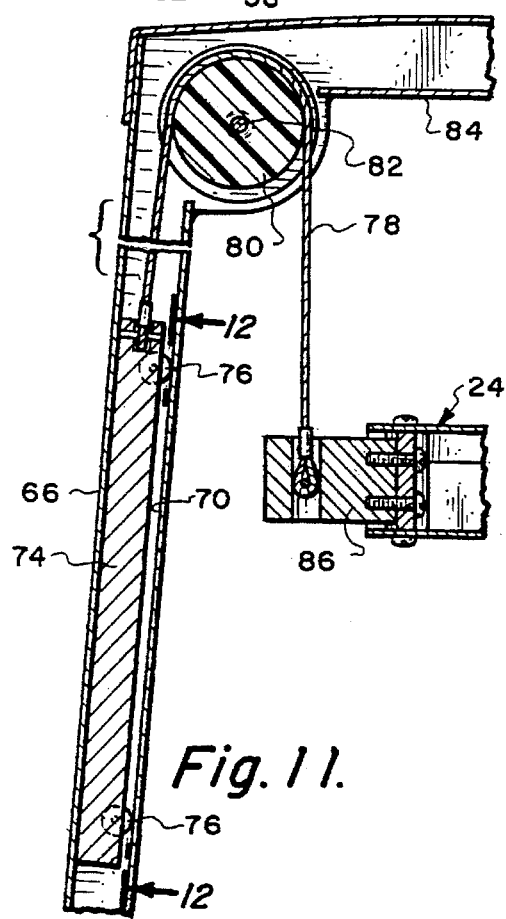
FIG. 11 is a cross-sectional view through one of the upstanding members of the base of the dissolution test apparatus of the present invention taken along line 11—11 of FIG. 4 showing the counterbalancing system that is used in conjunction with the dissolution test apparatus of the present invention.
Figure 12:
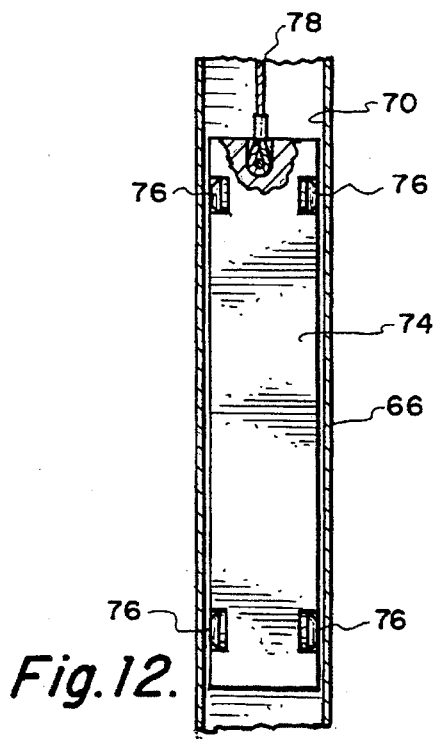
FIG. 12 is a partly in cross-sectional view showing in more detail one of the counterbalancing weights utilized in conjunction with the counterbalancing system that is incorporated within the dissolution test apparatus of the present invention taken along line 12—12 of FIG. 11.

Referring particularly to the drawings, there is shown the dissolution test apparatus 20 of this invention. The dissolution test apparatus 20 generally comprises a base 22, a drive head 24 and a frame 30. The frame 30 includes four in number of feet 26. The feet 26 are to rest on a supporting surface 28 which generally will comprise a table. The feet 26 are adjustably mounted on a frame 30. Separate from the frame 30 is a bath support 32. The bath support 32 includes an enlarged recess 34. The enlarged recess 34 is positioned substantially at the transverse middle of the bath support 32. The depth of the enlarged recess 34 is not sufficient to divide the bath support 32 into two separate halves. The result is the bath support 32 is in essence formed in two sections which are interconnected together by connecting bridge 36. Normally the frame 30, the bath support 32 and the connecting bridge 36 will be formed of rigid material such as steel or plastic.

The undersurface of the bath support 32 has mounted thereon a pair of foam pads 38. The foam pads 38 are also to be located on the supporting surface 28. One of the purposes of the foam pads 38 is to assist in diminishing the transmitting of vibration from the supporting surface 28 to the bath support 32.

Resting on the upper surface of the bath support 32 is a transparent rectangular bath 40. The bottom wall surface of the bath 40 includes a protrusion 42 which interlocks with the enlarged recess 34. This interlocking of the protrusion 42 with enlarged recess 34 fixes the position of the transparent rectangular bath 40 relative to the bath support 32 so that each time the transparent rectangular bath 40 is placed on the bath support 32 it is placed in precisely the same position. The transparent rectangular bath 40, normally constructed of plastic, has an internal chamber 44. This internal chamber 44 is to be filled with a liquid solution such as water, which is not shown. Water within the internal chamber 44 is to be constantly recirculated by a pump (not shown). Mounted through the wall of the transparent rectangular bath 40 is a water level sensor 46. The water level sensor 46 is connected to a control box 48. Information on the level of the water within the internal chamber 44 is then transmitted from the control box 48 to a printer (not shown). The readings on the water level are then to be made available to the control logic.

Also mounted to the wall of the transparent rectangular bath 40 is an electric heating coil 50. Associated with the heating coil 50 is a temperature sensor. The electric heating coil 50 is electrically connected by wire 52 to the control box 48. It is to be understood that the transparent rectangular bath 40 is to be removable from its mounting on the bath support 32 for purposes of emptying the liquid contents, cleaning of the transparent rectangular bath 40 and refilling of the internal chamber 44 with liquid. The electric heating coil 50 is to be used to maintain a precise temperature of the liquid within the transparent rectangular bath 40. Transparent rectangular bath 40 includes a drain plug 41 to facilitate removing of the liquid contents.

The transparent rectangular bath 40 is to be located beneath a platform 54. The platform 54 is peripherally supported on an enclosing frame 56. The enclosing frame 56 is fixedly mounted by short posts 58 onto the frame 30. Platform 54 is basically constructed of sheet metal and includes a plurality of spaced apart flask receiving ports (not shown). The ports are all of the same size and are evenly spaced apart. It is to be noted that there are eight in number of the ports mounted in the platform 54.

Mounted within each port is a centering ring 60. Each centering ring 60 is identical and generally will be constructed of a plastic material. The glass flask 62 is to be placed in conjunction with each centering ring 60 with the annular lip of the glass flask 62 resting on the centering ring 60. The body of the glass flask 62 extends within the internal chamber 44 and is submerged within the liquid contained therein. Each glass flask 62 is identical.

Mounted on the platform 54 are a plurality of clamp knobs 64 located directly adjacent the annular flange of the glass flask 62, Each clamp knob 64 is to be pivoted relative to the platform 54. It is the purpose of the clamp knobs 64 to be pivoted to be positioned over the annular flange of the glass flask 62 thereby securing in position each glass flask 62 to the platform 54. It is to be noted that there are two in number of clamp knobs 64 for each glass flask 62. It is to be understood that each glass flask 62 is to be filled to a precise level with a liquid which is not shown. The liquid which is contained within each glass flask 62 will generally be an acid since it is intended that this acid duplicate the acid contained within the human stomach.

Fixedly mounted on the frame 30 and extending substantially in a vertical orientation therefrom are a pair of spaced apart supporting posts 66 and 68. Supporting post 66 has a hollow interior chamber 70 with supporting post 68 also having a similar hollow interior chamber 72. Mounted within the hollow interior chamber 70 is a counterweight 74. Counterweight 74 has a plurality of wheels 76 mounted thereon, Wheels 76 are to ride against a wall surface of the hollow interior chamber 70. Counterweight 74 is free to move vertically within the supporting post 66, The upper end of the counterweight 74 is connected to one end of a cable 78. Cable 78 is conducted over a pulley 80. The pulley 80 is rotatably mounted by means of shaft 82 to crossbar 84. Crossbar 84 is secured between the supporting posts 66 and 68 and is located at the upper end of the supporting posts 66 and 68, The free end of the cable 78 is attached to block 86 which is fixedly mounted to the drive head 24, It is to be understood that contained within the hollow interior chamber 72 is a counterweight 88 which has wheels similar to wheels 76 which are not shown, These wheels ride against the wall surface of the hollow interior chamber 72, The counterweight 88 is connected to cable 90 which rides over a pulley 92. The pulley 92 is rotatably mounted by a shaft 94 to the crossbar 84. The opposite end of the cable 90 is connected to a block 91 which is similar to block 86 which is also mounted to the drive head 24. Cover assembly 240 is fixedly mounted on the drive head housing 114. Block 86 is fixedly mounted on arm 242. Block 91 is fixedly mounted on arm 244. Arms 242 and 244 are also fixedly mounted to the drive head housing 114. Arm 242 includes an opening 246 through which the vertical rod 102 is conducted and also where the movable brake arm 228 and fixed brake arm 230 are located.

The combined weight of the counterweights 74 and 88 is to equal the weight of the drive head 24. The drive head 24 is mounted to a pair of bearing sleeves 96 and 98. Incorporated within each of the bearing sleeves 96 and 98 are a pair of linear ball bearings 100 and 101 which is shown being located within bearing sleeve 96. Conducted through the bearing sleeve 96 is a vertical rod 102. The vertical rod 102 is mounted between base plate 54 and the crossbar 84. The ball bearings 100 and 101 facilitate low-frictional movement of the bearing sleeve 96 relative to the vertical rod 102. It is to be understood that a pair of ball bearings similar to ball bearings 100 and 101 is contained within the bearing sleeve 98 and these bearings are to facilitate low-frictional movement of the bearing sleeve 98 on the vertical rod 104. The vertical rod 104 is also mounted between the base plate 54 and the crossbar 84.

Fixedly mounted on the vertical rod 102 is a lower collar 108. The lower collar 108 functions as a stop to limit the movement of the drive head 24 in the downward direction. The collar 108 can be adjusted according to individual desires. There is also a lower collar 112 mounted on the vertical rod 104 for the same purpose. It is to be understood that collars 106 and 112 are in transverse alignment.

The drive head 24 has a drive head housing 114. The drive head housing 114 includes a manually operable control panel 116 which will permit activation of the dissolution test apparatus 20 of this invention. The manually operable control panel 116 also includes appropriate settings for performing other functions such as raising and lowering the temperature of the liquid contained within the transparent rectangular bath 40, varying the speed of the mixing paddles 126 which are to be described further on in the specification and also raising and lowering of the sample tubes which will also be described further on in the specification. Baskets (not shown) could be used instead of the mixing paddles 126. Also included within the drive head housing 114 is a readout screen 118. Appropriate numerical and/or word indicia is to be displayed corresponding to certain values such as the temperature level and time. Also included within the drive head housing 114 are a series of control buttons 120 which are to be activated to perform certain functions such as turning the dissolution test apparatus 20 on or off as well as performing numerous other functions.

Mounted on the undersurface of the drive head 114 are a plurality of chuck collets 122. It is to be noted that there are eight in number of the chuck collets 122. Removably mounted within each chuck collet 122 is a mixing paddle shaft 124. The outer end of the mixing paddle shaft 124 has fixedly mounted thereto a mixing paddle 126. The chuck collet 122 is threadably secured onto a collar 128. The collar 128 is fixedly mounted onto a spindle shaft 138. Tightening of the chuck collet 122 on the collar 128 will result tightly pressing of the sleeve 132 into engagement with the mixing paddle shaft 124 thereby securing the mixing paddle 124 to the chuck collet 122. The collar 128 is fixedly mounted onto the spindle shaft 138. The spindle shaft 138 is frictionally, rotationally and lineally mounted by means of bearing assemblies 134 and 136 relative to the extension 130. Mounted between the collar 128 and the bearing assembly 134 are washers 140. A similar set of washers 142 is located between the bearing assembly 136 and the driven pulley 144. Between the driven pulley 144 and the spindle shaft 138 there is freedom of rotation of the driven pulley 144. The driven pulley 144 is to be rotated by means of a drive belt 146. It is to be understood that there is a driven pulley 144 for each of the mixing paddle shafts 124. The extension 130 is mounted within the drive head housing 114 so that the longitudinal center axis of each extension 130 is precisely centrally located with the longitudinal center axis of a glass flask 62.

The upper surface of the driven pulley 144 includes a series of drive dogs 148. These drive dogs 148 are to engage with a series of drive teeth 150 that are formed within a drive dog unit 152. The drive dog unit 152 is mounted about the spindle shaft 138 and is fixed thereto. Manual lineal movement of the drive dog unit 152 is possible by placing of the user's fingers in connection with finger receiving annular recess 154 formed on the exterior surface of the drive dog unit 152. A coil spring 156 is mounted within annular chamber 158 formed within the drive dog unit 152. The outer upper end of the spindle shaft 138 is fixedly connected to a cap 160. The outer end of the coil spring 156 abuts against the cap 160.

With the drive dog unit 152 in the position shown in FIG. 10 of the drawings, a drive connection is established between the drive dog unit 152 and a screw 162. The screw 162 is fixedly mounted to the spindle shaft 138. However, upon a user grasping the drive dog unit 152 in the area of the finger receiving annular recess 154 and lineally moving in an upper direction the drive dog unit 152, the drive dogs 148 are disengaged from the drive teeth 150. Lineal movement of the drive dog unit 152 against the cap 160 will locate the screw 162 within the confines of an annular groove 164. The driven pulley 144 which is no longer being rotated has a driving connection with the spindle 138 and hence the mixing paddle shaft 124. There is to be incorporated an appropriate detent mechanism (not shown) in conjunction with the drive dog unit 152 that permits the drive dog unit 152 to be pivoted a few degrees and then remain locked in this disengaged position. This disengaged position is desirable by some users so that each mixing paddle shaft 124 can be engaged separately to initiate rotation precisely at a time when a pill is dropped into the liquid within a glass flask 62. Some users prefer this sequential operation of the mixing paddle shafts 124 so that each mixing paddle shaft 124 is operated at precisely the same time a pill is dropped within the glass flask 62. When a pill is so dropped within a glass flask 62, the operator then merely pivots in a reverse direction the drive dog unit 152 which will disengage such from the detent mechanism which will then cause the drive dog unit 152 to be moved by the bias of the coil spring 156 to engage the drive dogs 148 with the drive teeth 150 and locate the screw 162 spaced from the annular groove 164. It is to be understood that four in number of mixing paddle shafts 124 are driven by the drive belt 146. Mounted within the drive head housing 114 is an idler pulley 166 whose function is to maintain the drive belt 146 in a taut manner at all times.

The remaining four in number of the mixing paddle shafts 124 are rotated by means of a drive belt 168. The drive belt 168 also connects with an idler pulley 170 whose function is to maintain the drive belt 168 constantly taut. Drive belt 146 connects with a drive pulley 172. Drive belt 168 connects with a drive pulley 174. Pulleys 172 and 174 are connected together by means of a drive belt 176. Drive belt 176 is maintained in driving connection with the drive pulleys 172 and 174 by means of the idler pulleys 178 and 180. An adjustable idler pulley 182 is adjustably mounted onto the drive head housing 114. The position of the adjustable idler pulley 182 can be adjusted to vary the pressure against the drive belt 176 to thereby insure that the drive belt 176 is maintained taut. The drive belt 176 is connected to motor operated pulley 184. The motor operated pulley 184 connects to the drive shaft 186 of a motor (not shown) the speed of which is controlled by the control box 48. The motor that operates the motor drive shaft 186 is mounted within motor housing 212. Varying the speed of the motor is accomplished by the user through the use of the manually operable control panel 116.

Mounted within the drive head housing 114 are a plurality of sample tubes 188. There is to be a sample tube 188 located directly adjacent each mixing paddle shaft 124 and slightly spaced therefrom. Each sample tube 188 is entirely hollow. The sample tube 188 terminates in a tip 190. Mounted on the tip 190 is a filter 192. Liquid is to be drawn through the filter 192 and into the sample tube 188. With the filter 192 located within the liquid of a glass flask 62, the liquid is to be movable through the sample tube 188 and into discharge tube 194 to be deposited within an appropriate container (not shown) to be tested to determine the amount of drug that has been dissolved within the liquid contained within the glass flask 62 from a pill (not shown) that has been deposited within the glass flask 62. It is to be understood that each aliquot that is removed from the discharge tube 194 is to be a precise amount and is to be located individually in an appropriate separate collecting container. Therefore the amount of drug that is dissolved within each glass flask 62 over time can be individually ascertained.

The drawing of the aliquot through the sample tube 188 can be accomplished by means of a vacuum source (not shown). After the correct amount of liquid has been removed by means of the sample tube 188, air is to be blown through the sample tubes 188 completely dispensing any remaining liquid contained within the sample tubes 188 back into the glass flasks 62. The discharge tubes 194 are each mounted within a separate connector 196. Each separate connector 196 is threadably secured onto a connecting sleeve 198 with there being a separate connecting sleeve 198 for each connector 196. Each connecting sleeve 198 is in turn threadably mounted onto a connector 200 which is fixed to the sample tube 188.

Each sample tube 188 is to be independently movable between a lower position (sampling position) locating the filter 192 within a glass flask 62 to an upper position (non-sampling position) with the filter 192 being spaced from the interior of its respective flask. This movement of each of the sampling tubes 188 is achieved by means of an air cylinder 202 with there being a separate air cylinder 202 for each sampling tube 188. The air cylinders 202 are mounted to the drive head housing 114. Operation of the air cylinders 202 is by means of air being supplied through rubber supply tube 204. Each air cylinder 202, when operated, lineally moves its respective shaft 206. Shaft 206 is connected to arm 208. Arm 208 is fixedly mounted on the sample tube 188. Air pressure is to be supplied through the rubber tubes 204 simultaneously so that each air cylinder 202 for each sample tube 188 is operated at the same time. Air pressure is to be supplied from a source (not shown) through fitting 210 to cause the movement of the sample tubes 188 simultaneously for all eight glass flasks 62.

The drive head 24, as previously discussed, is lineally movable on the vertical rods 102 and 104 within the confines of the collars 108 and 112. Also as previously discussed, the drive head 24 is counterbalanced by the counterweights 74 and 78. When the drive head 24 is moved to a lower position, at which time each mixing paddle 126 is located within a glass flask 62, it is desirable to fix into position the drive head 24. Also, when the drive head 24 is moved to the upper position and the mixing paddles 126 are spaced from their respective flasks, it is also desirable to have the drive head 24 to be again fixed in position. In order to fix in position the drive head 24, there is utilized a brake unit.

The brake unit is composed of a manually operated lever 214. The manually operated lever 214 is to be manually squeezable by a hand of the user so that the lever 214 is pivoted toward handle 216. The manually operated lever 214 is pivotally mounted by pivot pin 218 on the drive head housing 114. The pivoting movement of the manually operated lever 214 is indicated by arrow 220 of FIG. 13. The direction of movement in the squeezing motion of the manually operated lever 214 is indicated by arrow 222.

Extending from the manually operated lever 214 is a protrusion 224. Connected by bolts 221 to protrusion 224 is a plate 223. A cable 226 is clamped between protrusion 224 and plate 223. Cable 226 is fixed to movable brake arm 228. Movable brake arm 228 is pivotally mounted to fixed brake arm 230 by means of pivot pin 232. In between the brake arms 230 and 228 is located the vertical rod 102. Between the drive head housing 114 and the movable brake arm 228 is located a coil spring 234. The arms 228 and 230 function together as a caliper-type clamp. With the manually operated lever 214 normally at rest, the coil spring 234 forces the movable arm 228 into tight abutting contact with the vertical rod 102 clamping the vertical rod 102 in between the arms 228 and 230 thereby fixing the position of the drive head 24 on the vertical rod 102. However, when the user pivots the manually operated lever 214 toward the handle 216, the coil spring 234 is compressed and the movable brake arm 228 is displaced slightly from the vertical rod 102 as is clearly shown in FIG. 13 of the drawings. This will now permit free sliding movement of the drive head 24 relative to the vertical rods 102 and 104.

The braking force can be adjusted by the position of the stop bolt 236 which is mounted within the block 86. The brake arm 230 abuts against the stop bolt 236. Therefore, if there is inadequate braking force, it is only necessary to outwardly thread slightly the stop bolt 236 which will move brake arm 230 toward vertical rod 102 which will result in increasing the amount of braking force. Once the desired position of the stop bolt 236 is obtained, the nut 238 is tightened to thereby fix into position the stop bolt 236.

What is claimed is:

1. The dissolution test apparatus comprising:

a base, at least one flask mounted on said base, said flask adapted to contain a quantity of liquid;

a drive head located directly adjacent said base, said drive head movable relative to said base between a lower position and an upper position, a mixing paddle mounted on said drive head, with said drive head in said lower position the said mixing paddle is to be positioned within the confines of said flask, with said drive head in said upper position the said mixing paddle is spaced from said flask;

a handle mounted on said drive head, said handle to be used to manually move said drive head relative to said base;

brake means mounted on said drive head, said brake means connecting with said base, said brake means being manually movable by moving of a brake lever between a braking position and a release position, said brake lever being pivotally mounted on said drive head, said release position permitting movement of said drive head between said upper and said lower positions, said braking position fixing said drive head on said base, said brake lever being mounted directly adjacent said handle with manual operation of said brake lever to said release position being required prior to initiating manual movement of said drive head, whereby the position of said mixing paddle relative to said flask can be controlled by operation of said brake means; and said brake means comprising a frictional, grabbing caliper assembly that normally is located in a braking position due to spring force of a spring, said caliper assembly comprising a movable brake arm and a fixed brake arm, said base includes a vertical rod, said vertical rod being located between said movable brake arm and said fixed brake arm, locating of said brake lever in said braking position tightly frictionally connects said movable brake arm to said vertical rod, said brake lever being spaced from said movable brake arm, said brake lever being connected by a cable to said movable brake arm, movement of said brake lever moves said movable brake arm.

2. The dissolution test apparatus as defined in claim 1 wherein:

adjustment means for adjusting the position of said fixed brake arm relative to said vertical rod, whereby the closer the position said fixed brake arm is to said vertical rod the greater the braking force, whereby the farther the position said fixed brake arm is from said vertical rod the less the braking force.

* * * * *